(12) United States Patent
Neukirchen et al.

(10) Patent No.: US 12,138,481 B2
(45) Date of Patent: Nov. 12, 2024

(54) FAST GENERATION OF MULTI-LEAF COLLIMATOR (MLC) OPENINGS USING HIERARCHICAL MULTI-RESOLUTION MATCHING

(71) Applicant: Elekta Inc., Atlanta, GA (US)

(72) Inventors: Christoph Neukirchen, Aachen (DE); Alfonso Agatino Isola, Eindhoven (NL); Harald Sepp Heese, Hamburg (DE); Torbjoern Vik, Hamburg (DE); Rolf Jürgen Weese, Norderstedt (DE); Matthieu Frédéric Bal, Geldrop (NL)

(73) Assignee: Elekta Inc., Atlanta, GA (US)

( * ) Notice: Subject to any disclaimer, the term of this patent is extended or adjusted under 35 U.S.C. 154(b) by 464 days.

(21) Appl. No.: 17/601,121

(22) PCT Filed: Mar. 27, 2020

(86) PCT No.: PCT/EP2020/058636
§ 371 (c)(1),
(2) Date: Oct. 4, 2021

(87) PCT Pub. No.: WO2020/201037
PCT Pub. Date: Oct. 8, 2020

(65) Prior Publication Data
US 2022/0168592 A1 Jun. 2, 2022

Related U.S. Application Data

(60) Provisional application No. 62/829,066, filed on Apr. 4, 2019.

(51) Int. Cl.
*A61N 5/10* (2006.01)
*G16H 20/40* (2018.01)
*G16H 30/20* (2018.01)

(52) U.S. Cl.
CPC ......... *A61N 5/1036* (2013.01); *A61N 5/1047* (2013.01); *G16H 20/40* (2018.01); *G16H 30/20* (2018.01)

(58) Field of Classification Search
None
See application file for complete search history.

(56) References Cited

U.S. PATENT DOCUMENTS 9,393,442 B2   7/2016 Isola
10,675,483 B2  6/2020 Vik
(Continued)

OTHER PUBLICATIONS

International Search Report and Written Opinion of PCT/EP2020/058636, dated May 28, 2020.
(Continued)

*Primary Examiner* — Marcus H Taningco
(74) *Attorney, Agent, or Firm* — Schwegman Lundberg & Woessner, P.A.

(57) ABSTRACT

A device for optimizing a radiation therapy plan (30) for delivering therapeutic radiation to a patient using a therapeutic radiation source (16) while modulated by a multi-leaf collimator (MLC) (14) includes at least one electronic processor (25) connected to a radiation therapy device (12). A non-transitory computer readable medium (26) stores instructions readable and executable by the at least one electronic processor to perform a radiation therapy plan optimization method (102) including: optimizing MLC settings of the MLC respective to an objective function wherein the MLC settings define MLC leaf tip positions for a plurality of rows of MLC leaf pairs at a plurality of control points (CPs). The optimizing is performed in two or more iterations with a resolution of the MLC settings increasing in successive iterations.

19 Claims, 4 Drawing Sheets

(56) References Cited

U.S. PATENT DOCUMENTS

| | | | |
|---|---|---|---|
| 2006/0045238 | A1 | 3/2006 | Nguyen |
| 2012/0043482 | A1 | 2/2012 | Prince |
| 2017/0087384 | A1 | 3/2017 | Nord |
| 2019/0083816 | A1* | 3/2019 | Menichelli ........... A61N 5/1081 |
| 2019/0388709 | A1* | 12/2019 | Isola ........................ A61N 5/10 |

OTHER PUBLICATIONS

Otto, Karl "Volumetric Modulated Arc Therapy: IMRT in a Single Gantry Arc", Medicla Physics, vol. 35, No. 1, 2007, pp. 310-317.
Scherrer, Alexander et al "IMRT Planning on Adaptive Volume Structures—a Decisive Reduction in Computational Complexity", Physics in Medicine and Biology, vol. 50, 2005, pp. 2033-2053.
Oliver, Mike et al "Analysis of RapidArc Optimization Strtegies using Objective Function Values and Dose-Volume Histograms", Journal of Applied Clinical Medical Physics, vol. 11, No. 1, 2010.
Vanetti,Engenio et al "On the Role of the Optimization Algorithm of RapidArc Volumetric Modulated Arc Therapy on Plan Quality and Efficiency", Medical Physics, vol. 38, No. 11, 2011.

* cited by examiner

FAST GENERATION OF MULTI-LEAF COLLIMATOR (MLC) OPENINGS USING HIERARCHICAL MULTI-RESOLUTION MATCHING

CROSS-REFERENCE TO PRIOR APPLICATIONS

This application is the U.S. National Phase application under 35 U.S.C. § 371 of International Application No. PCT/EP2020/058636, filed on Mar. 27, 2020, which claims the benefit of U.S. Provisional Patent Application No. 62/829,066, filed on Apr. 4, 2019. These applications are hereby incorporated by reference herein.

FIELD

The following relates generally to radiation therapy arts, radiation therapy plan optimization arts, to conversion of a radiation therapy plan defined by beam parameters into physically realizable parameters such as multi-leaf collimator (MLC) settings, and related arts.

BACKGROUND

For external photon beam radiation therapy (RT), the creation of suitable openings defined by the MLC is a central component in a Treatment Planning System (TPS). Different MLC opening configurations are applied in some variations for different treatment modalities and optimization types, e.g.: for volumetric modulated arc therapy (VMAT); Direct Machine Parameter Optimization (DMPO); Leaf Sequencing; etc. The MLC settings are optimized for each individual patient in order to optimally deliver radiation to the target (usually a malignant tumor) while limiting undesirable radiation exposure to any neighboring critical organs (sometimes also referred to as organs at risk, or OARs). In conventional RT, the radiation source is moved in a stepwise fashion around the patient, and the MLC settings are optimized at each position so that the time-integrated radiation exposure meets various objectives designed by medical professional (for example, a collaboration of an oncologist and a dosimetrist). In a continuous arc RT approach such as VMAT, the radiation source is moved continuously over an arc of up to 360°. To perform the continuous arc RT plan optimization, the continuous arc is discretized into a number of control points (CPs) which can then be treated analogously to the stepped positions of conventional RT planning. For example, some radiotherapy planning systems produce a plan in a Digital Imaging and Communications in Medicine (DICOM) format. The DICOM standard only allows to define leaf positions of an MLC at a sequence of beam positions in a discrete way, and can also be used in the planning system itself. It will be appreciated that to achieve sufficient resolution the number of CPs may be relatively large. A higher number of CPs includes a finer angular sampling rate, which increases the number of parameters that can be adjusted to improve the RT plan characteristics. During dose computation, a finer angular sampling reduces an error from approximating a continuous delivery into discrete gantry positions.

A typical MLC consists of multiple rows of leaf pairs (and optionally has some larger blocker elements). Positions of the leaf tips can be controlled individually. The leaf tip positions are governed by some range constraints which are defined statically or dynamically (e.g., based on the specification of the MLC, the gantry mechanics, and the treatment modality). When performing the MLC optimization, the position of each leaf tip of the MLC at each CP is a parameter, so that the total number of parameters to be optimized is very large. In certain two-step optimization approaches, the beam shape at each CP is defined by a set of virtual beamlets which are optimized so that the time integrated radiation dose distribution delivered to the patient meets various clinical objectives (e.g. objectives pertaining to minimum dose delivered to the target and objectives pertaining to maximum dose delivered to critical organs); then, the MLC settings are optimized to achieve the desired beamlets. In single-pass approaches such as DMPO, the MLC settings are directly optimized respective to the clinical objectives. RT plans with a large number of variables can be optimized using a column generation approach that iterates between Fluence Map Optimization (FMO) and segment openings (re-)generation based on the resulting incidence fluence.

For VMAT, in particular, the accuracy and computational speed of opening generation is essential in the treatment planning process because of the very large number of control points to consider. In VMAT, the motion of MLC leaves along the treatment arcs is modelled as sequence of discrete control points. Each control point is associated with a particular MLC opening. The sequence of control points along each arc follows a predefined angular resolution, typically at 4° or 2°. Given such a setup, the number of openings to optimize in a VMAT scenario that involves multiple arcs is in the order of some hundreds.

In general, the task of creating an opening for a control point in a treatment delivery scenario typically constitutes a problem of computing an approximating fit to an ideal target fluence given some boundary conditions. Such approximating fit (e.g. in a Least Squares sense) may be implemented in several ways depending on the modelling type for the leaf tips in the MLC and for the corresponding opened field in between. Based on the requirements of systems to define leaf positions at a certain precision, a practical approach includes a model for the MLC leaves is a discrete spatial grid that defines feasible leaf tip positions. For such grid model the solution space of the optimal MLC fitting problem is the potentially very large discrete set of feasible MLC openings (e.g., depending on the grid size). An optimal MLC opening is found by performing pattern matching between the photon fluence formed by the hypothetical leaf pair openings against an ideal target fluence. In a two-step optimization, the ideal target fluence is typically obtained by a FMO that precedes the MLC opening optimization step, and FMO might consider the fluence from the other control points in the current state of the treatment plan. In a DMPO approach, the MLC openings are directly optimized to achieve the target fluence.

For opening creation in a typical MLC system, the optimal fit of a multi-row opening against the 2-D target fluence map is to be obtained; this involves computing matching scores at individual rows for all feasible leaf pair openings according to the grid model. To obtain a final overall fitting criterion the individual matching scores in each MLC row must be combined properly. In addition, further quantities e.g. those related to adjacent leaf rows (to control and regularize the properties of the opening contour formed by the opened leaf pair rows) might contribute to the overall fitting criterion as well. Global optimization methods, e.g. based on a shortest-path graph search algorithm are an efficient means to determine the best fitting opening amongst the large set of feasible MLC openings according to such criteria.

In today's high-throughput clinical operation of semi-automated RT treatment planning (that still usually requires some manual interaction by the treatment planning staff), a rapid assessment of final plan optimization results is demanded. Hence, availability of very fast computational methods for treatment plan optimization (which typically includes multiple steps of MLC opening creation) is essential for practical use of TPS.

The following discloses new and improved systems and methods to overcome these problems.

SUMMARY

In one disclosed aspect, a device for optimizing a radiation therapy plan for delivering therapeutic radiation to a patient using a therapeutic radiation source while modulated by a MLC includes at least one electronic processor connected to a radiation therapy device. A non-transitory computer readable medium stores instructions readable and executable by the at least one electronic processor to perform a radiation therapy plan optimization method including: optimizing MLC settings of the MLC respective to an objective function wherein the MLC settings define MLC leaf tip positions for a plurality of rows of MLC leaf pairs at a plurality of CPs. The optimizing is performed in two or more iterations with a resolution of the MLC settings increasing in successive iterations.

In another disclosed aspect, a non-transitory computer readable medium stores instructions executable by at least one electronic processor to perform a radiation therapy plan optimization method. The method includes: optimizing MLC settings of an MLC of a radiation therapy device respective to an objective function in which the MLC settings define MLC leaf tip positions for a plurality of rows of MLC leaf pairs at a plurality of CPs along the arc. The optimizing is performed in two or more iterations with a resolution of the MLC settings increasing in successive iterations. The optimizing includes both increasing a resolution of leaf tip positions in successive iterations and increasing a number of rows of MLC leaf pairs in successive iterations.

In another disclosed aspect, a radiation therapy plan optimization method includes: optimizing MLC settings of an MLC of a radiation therapy device respective to an objective function in which the MLC settings define MLC leaf tip positions for a plurality of rows of MLC leaf pairs at a plurality of CPs along the arc; and delivering therapeutic radiation to the patient using a therapeutic radiation source of the radiation therapy device traversing the arc while modulated the MLC in accordance with a radiation therapy plan. The optimizing is performed in two or more iterations with a resolution of the MLC settings increasing in successive iterations;

One advantage resides in generating a RT plan with an accurate dose delivery.

Another advantage resides in utilizing a fine MLC grid to optimize positions of MLC leaves.

Another advantage resides in rapidly producing an optimized RT plan with optimized MLC leaf positions.

Another advantage resides in generating precise MLC leaf positioning by utilizing a high-resolution MLC grid (and angular grid for VMAT delivery) while still maintaining a fast computation speed in the multi-row opening creation process.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

The following relates to radiation therapy planning. This entails two steps. First, FMO is performed. This optimizes the fluence profile at each control point (CP), thus generating a fluence map for each control point. However, the fluence map is not physically realizable. Thus, in a second step, the fluence map at each CP is converted to settings of the leaves of a MLC. In a variant optimization process—DMPO—the MLC settings are directly optimized against the clinical objective function, based on gradients of dose-based objectives for leaf sequencing. There are various possible combinations/sequences, e.g. initial rough MLC settings optimization based on clinical objective followed by FMO and back-and-forth.

Each MLC includes a number of rows of leaf pairs. In other words, each row of the MLC has two MLC leaves, and an opening is defined between the facing ends of the two leaves (unless the ends are brought into contact so as to completely close the opening). By sliding the leaves along the row, this opening can be set larger or smaller, and can be positioned along the row or under a jaw of the MLC.

For planning purposes, the continuous arc employed in a technique such as VMAT is discretized a large number of CPs, e.g. at 2° to 4° increments in some examples. By concurrently optimizing the MLC settings at all CPs, imperfect matching of the fluence map (from step 1) at a first CP could be compensated by imperfect matching of the intended fluence map at a second CP in a way that compensates the imperfect fluence map matching at the first CP. The MLC settings optimization is usually iterative and in the two-step approach uses the overall fluence map as the objective function. In an approach like DMPO, the MLC settings optimization may use the clinical objectives as the objective function.

Accurate dose delivery is an essential goal for high quality treatment planning. This makes a precise and highly resolved placement of MLC leaf tips mandatory. In the case of utilizing a discrete MLC grid model for leaf positioning such requirement demands for a high-resolution grid spacing. However, a finer MLC grid spacing yields a larger number of different hypothetical leaf pair openings that are involved in the matching process during opening creation. Such growth of solution space can make the pattern matching a time-consuming step in the automatic optimization during treatment planning.

The following discloses improving efficiency of the MLC optimization by using coarse-to-fine resolution sequences. In one aspect, the MLC leaf tips of each row are initially optimized over their entire dynamic range using a coarse grid. In the next pass, the optimization is over a smaller sub-set of that range using a finer grid; and so forth until the finest physically realizable grid resolution is reached. Optimization sequences have found that this approach provides results that are similar to that achieved using finest resolution from the start in most cases.

In some embodiments disclosed herein, the coarse-to-fine approach can be used in the "vertical" direction (that is, the direction transverse to the length of the row), by grouping several adjacent MLC leaf rows together to coarsen the resolution in the vertical direction.

In other embodiments disclosed herein, the coarse-to-fine approach can be used in the angular direction, by grouping together several CPs that are adjacent along the arc to coarsen the resolution along the arc.

The coarse-to-fine sequence approach can be used independently in any one, two, or all three of these dimensions. The coarser positioning not only makes the leaf sequencing faster (i.e., with less possibilities to explore) but potentially also the dose calculation as well.

In further embodiments disclosed herein, the option of using an MLC opening characteristic or quality as an objective in the MLC settings optimization is utilized. In general, optimized MLC settings that produce a ragged edge to the opening due to vertically adjacent MLC leaf rows having large differences in their tip positions are undesirable. Similarly, a zigzag edge of the opening is undesirable. In principle, these opening characteristics can be enforced (in a soft sense) by adding appropriate MLC opening objectives in the optimization. Such objectives can also be included in combination with the coarse-to-fine optimization sequences disclosed herein. However, the coarse-to-fine optimization sequence can naturally bias toward smoother opening edges, since for example when the optimization transitions from grouping (for example) 12 rows in the vertical direction together to grouping (for example) 4 rows in the vertical direction together, the rows of the original group of 12 will have identical tip positions at the start of the 4-rows resolution optimization.

Figure 1:
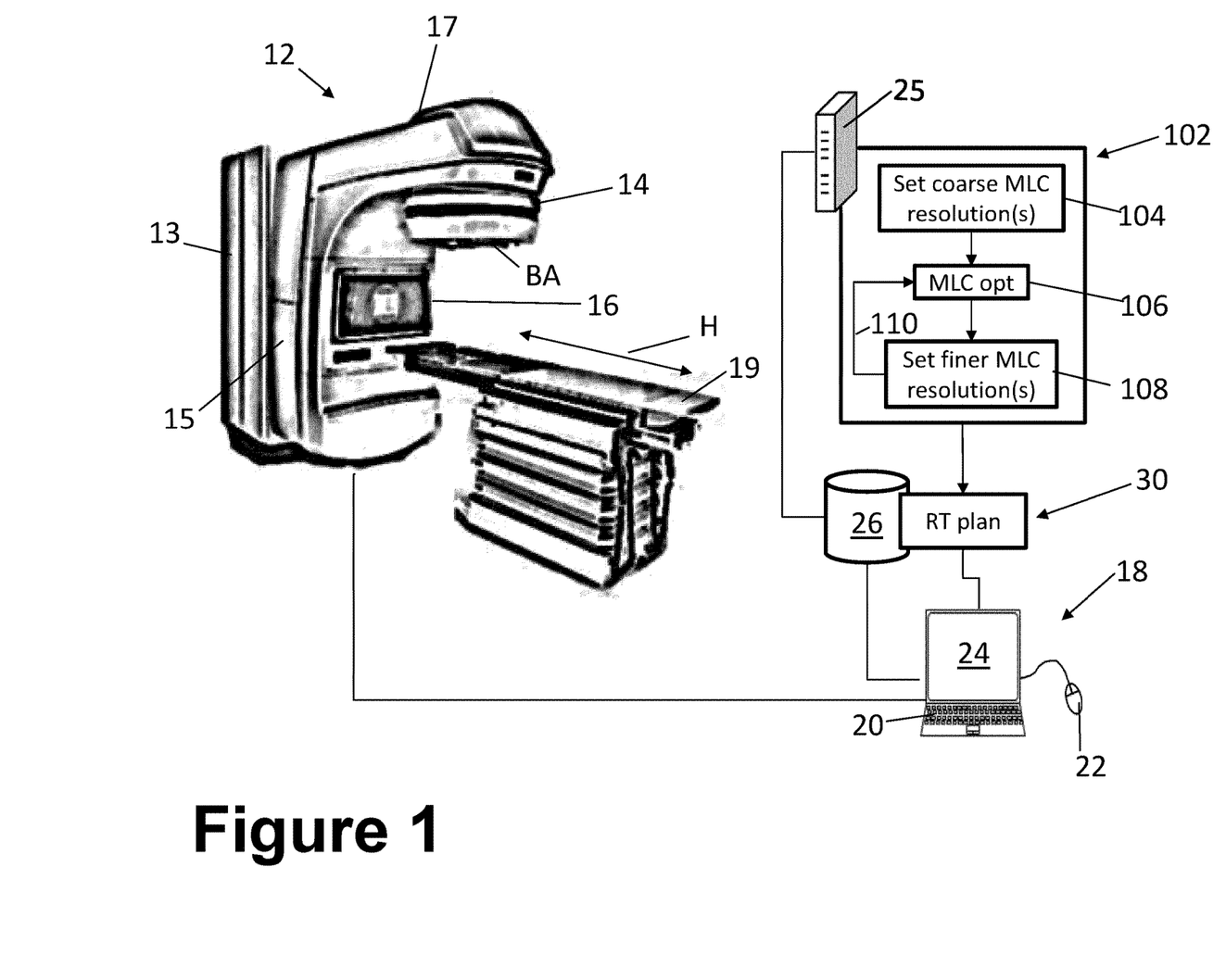
FIG. 1 diagrammatically a radiation delivery planning optimization system according to one aspect.

With reference to FIG. 1, an illustrative embodiment of a radiation delivery planning optimization system is shown. The radiation therapy may be any type of radiation therapy employing therapeutic radiation beams, e.g. electron beams, proton beams, high energy X-ray beams, or so forth. The radiation treatment may employ a discrete "step-and-shoot" approach in which a radiation beam source is stepped between successive fixed positions along a trajectory that partially or entirely encircles the patient. Alternatively, the radiation treatment may employ a continuous arc radiation therapy, such as VMAT, Intensity Modulated Arc Therapy (IMAT), step and short RT delivery, or so forth, in which the radiation beam source continuously irradiates the patient as the beam is revolved around the patient along a partially or entirely encircling trajectory. For example, the traversing of the trajectory comprises moving a therapeutic radiation source along a continuous arc. The number of beams may be one, two, three, or more. In the case of continuous arc radiation therapy, the number of arcs executed in the therapy session may, in general, be one, two, three, or more. For planning purposes, a continuous arc is discretized into discrete control points, e.g. at 2 to 4 intervals (intervals larger or smaller than this are also contemplated, depending upon the desired resolution). In other examples, the trajectory may be circular, non-circular, or otherwise-shaped, and may be traversed in a step and shoot approach or continuously. In the latter case, the continuous trajectory is typically discretized into control points along the trajectory in order to make the radiation therapy planning more tractable.

Figure 2:
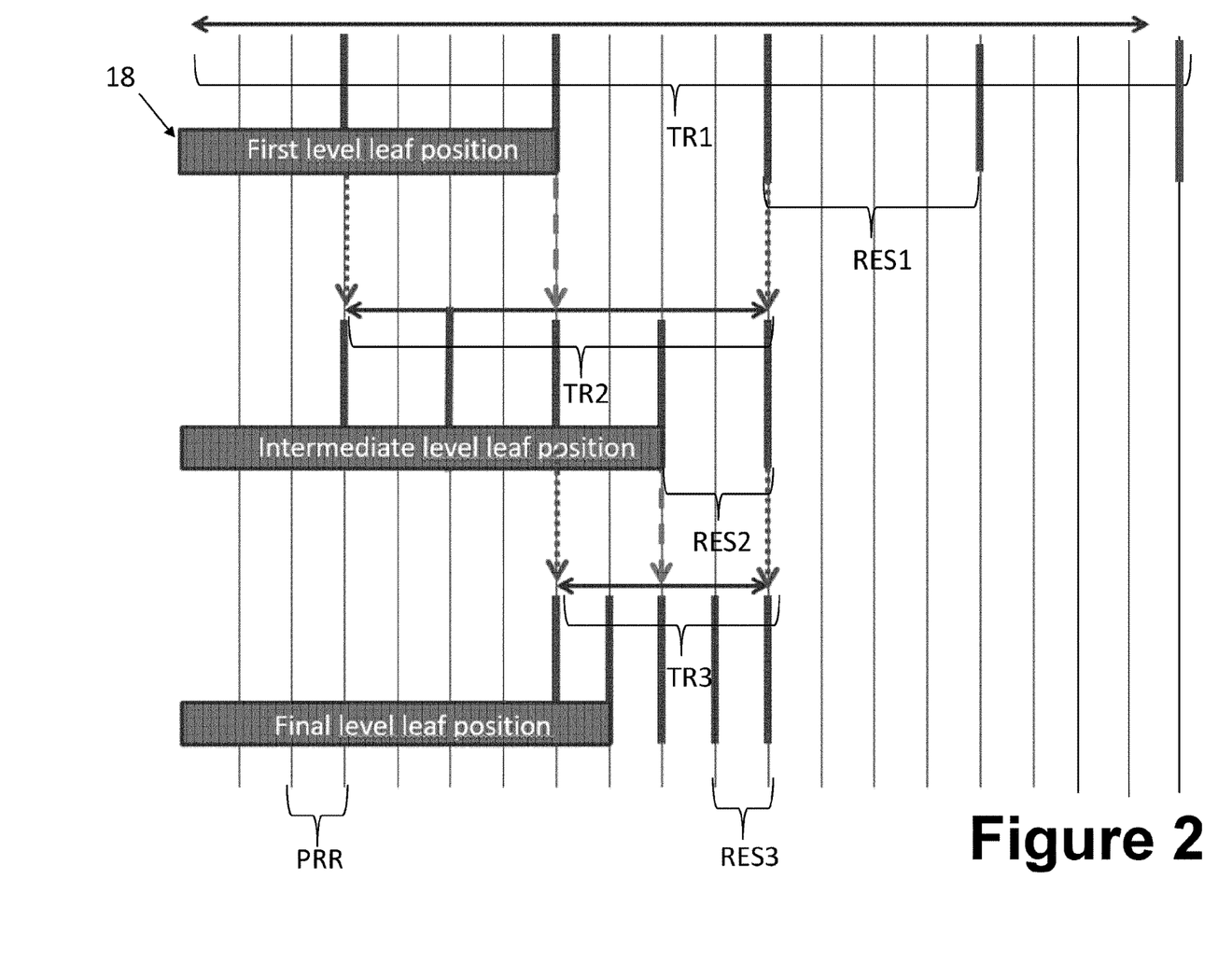
FIGS. 2-4 diagrammatically show different embodiments of optimizing positions of leaves of an MLC of the system of FIG. 1.
Figure 3:
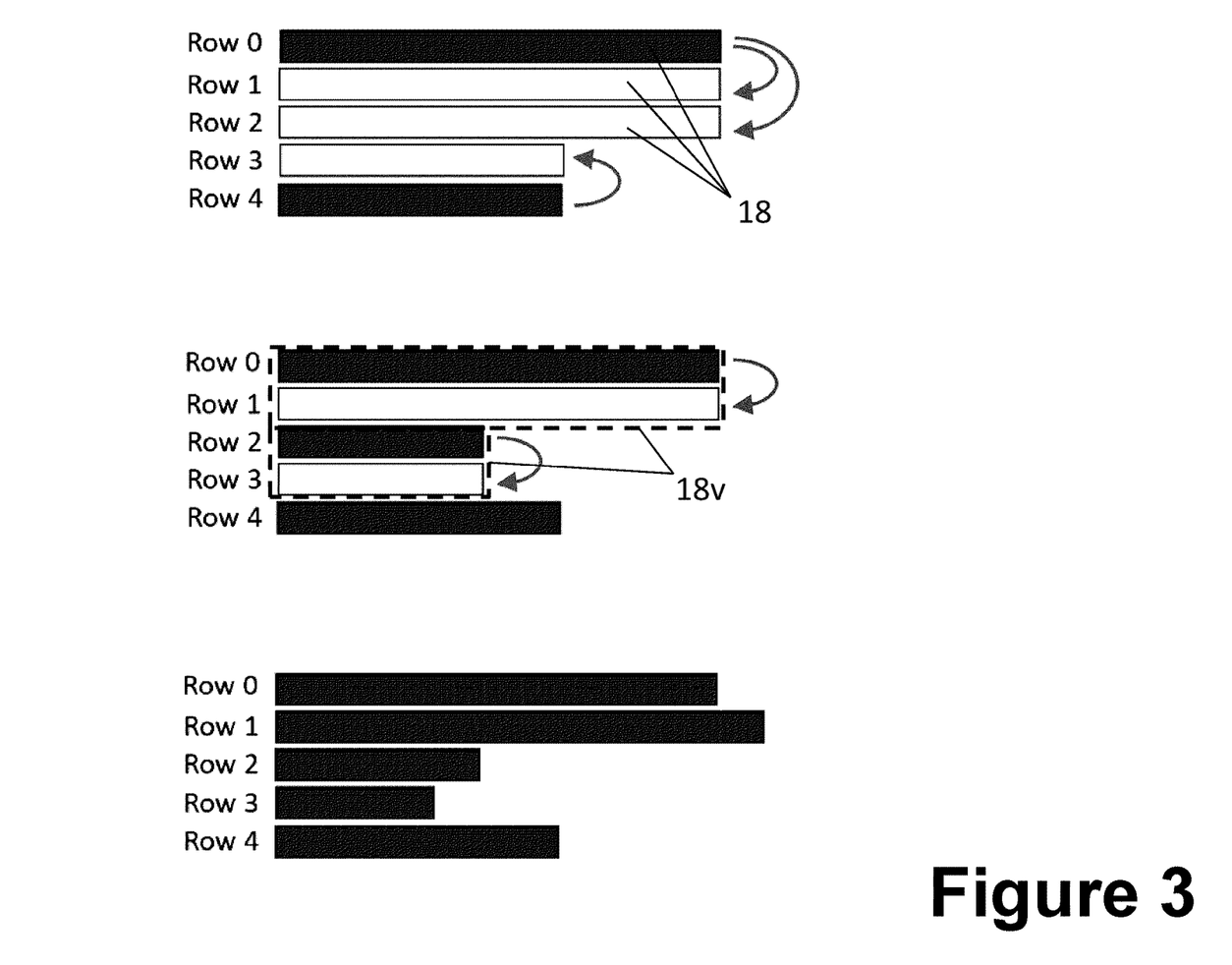
Figure 4:
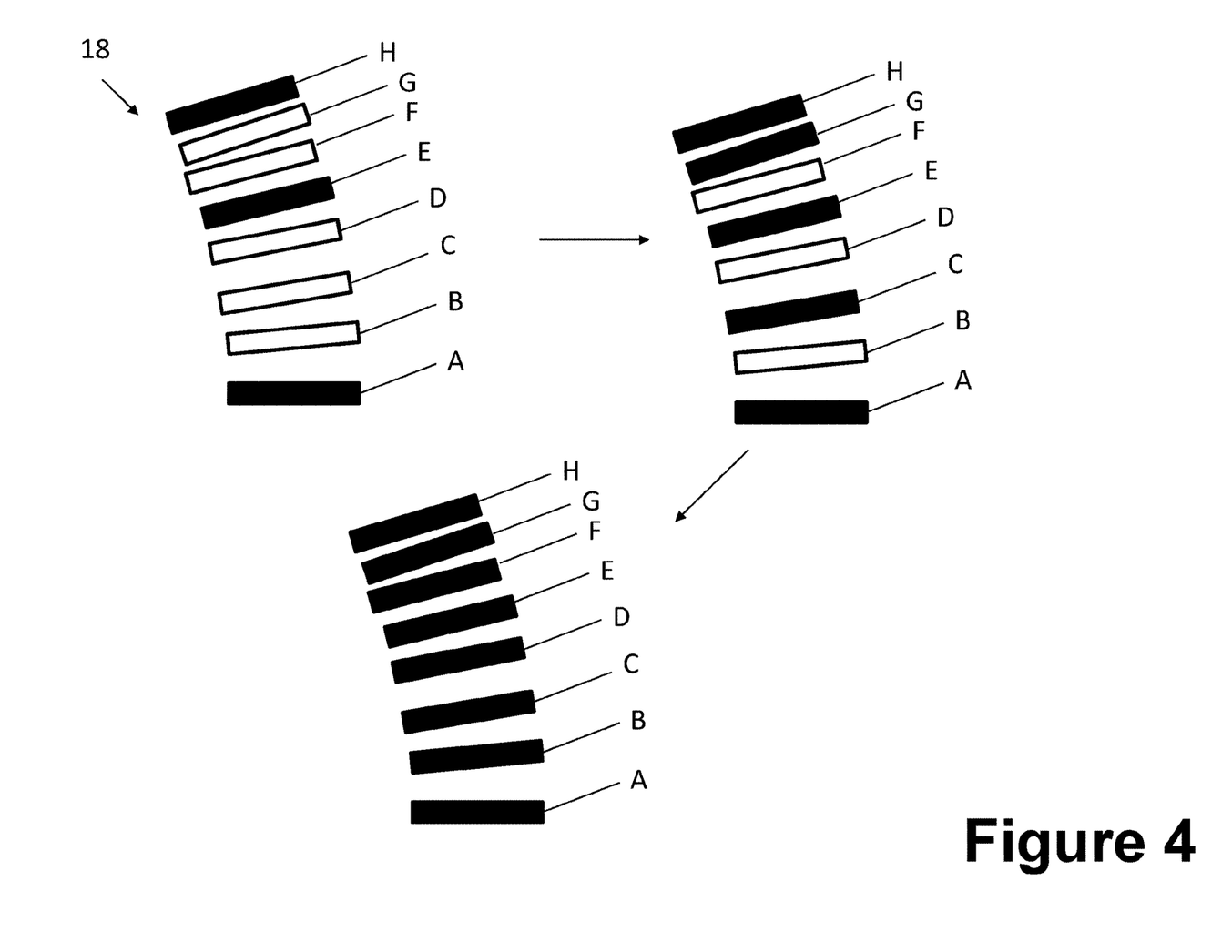

In one example, the radiation delivery planning optimization system can be a linear accelerator (LINAC) 12 with a multi-leaf collimator (MLC) 14 configured to shape and deliver a high energy electron beam that strikes a target (e.g., an x-ray or gamma ray generator and associated hardware which serves as a radiation source 16) that emits x-rays (i.e., photons) in response, resulting in a therapeutic beam delivered to a patient (not shown). The MLC 14 includes a beam aperture BA formed by a plurality of MLC leaves (details of which are shown in FIGS. 2-4) grouped in pairs that are adjustable to be set to shape the radiation beam during the radiation treatment. The LINAC 12 includes a fixed base 13 supporting the LINAC, and a gantry portion 15 mounted to the base 13 with an arm 17 that rotates around a horizontal axis H of a patient (not shown) lying on a table or couch 19. In some embodiments, the couch 19 provides three degrees of translational freedom of movement and optionally also three degrees of rotational freedom of movement, with couch position settings optionally being parameters of a parameterized radiation treatment plan to be executed by the radiation delivery planning optimization system 10. A therapeutic radiation beam is emitted from the LINAC 12 and passes through (and is shaped by) the MLC 14 in an orientation towards the table 19 (e.g., downward as shown in FIG. 1). For a trajectory comprising a continuous arc to deliver RT, the arm 17 rotates around the axis H to deliver the therapeutic radiation to the patient over the range of angles making up the arc, and as it rotates the leaves of the MLC 14 open and close in accordance with a predetermined radiation therapy plan in order to modulate the shape of the therapeutic radiation beam at the various angles (modelled in the plan as control points, CPs) of the arc.

The radiation therapy delivery device 12 also includes (or is controlled by) a computing device 18 (e.g., typically a workstation computer, or more generally a computer, although another form factor such as a tablet, a smartphone, and so forth is also contemplated). The workstation 18 comprises a computer or other electronic data processing device with typical components, such as at least one electronic processor 20, at least one user input device (e.g., a mouse, a keyboard, a trackball, and/or the like) 22, and a display device 24. In some embodiments, the display device 24 can be a separate component from the computer 18. The RT planning is typically performed on a computer 25 with high computing capacity, such as a server computer accessed via a hospital network. While a single server 25 is illustrated, it will be appreciated that the desired computing capacity may be obtained by way of a plurality of cooperating server computers, e.g. a computing cluster, cloud computing resource, or so forth, and it is to be understood that the computer 25 encompasses such multi-computer embodiments.

One or more non-transitory storage media 26 are also provided to store data and instructions (e.g. software) that are readable and executable by the computer 25 to perform RT planning as disclosed herein, and/or executable by the workstation or other controller 18 to control the RT delivery device 12 to deliver therapeutic radiation to the patient in accordance with the plan. The non-transitory storage media 26 may, by way of non-limiting illustrative example, include one or more of a magnetic disk, RAID, or other magnetic storage medium; a solid-state drive, flash drive, electronically erasable read-only memory (EEROM) or other electronic memory; an optical disk or other optical storage; various combinations thereof; or so forth. The storage media 26 may comprise a plurality of different media, optionally of different types, and may be variously distributed (e.g. a hard drive installed in the workstation 18, a RAID accessed via the hospital network, and/or so forth. An optimized RT plan 30 generated by the server 25 is suitably stored on the non-transitory storage media 26 and later downloaded by the workstation 18 and the LINAC 12 controlled in accordance with the RT plan 30 to deliver therapeutic radiation to the patient. In another example, the optimized RT plan 30 is transferred in DICOM format to and from an oncology information database (not shown), the radiation delivery planning optimization system 10, a PACS database (not shown), among others. As noted, the non-transitory storage media 26 also stores instructions readable and executable by the at least one electronic processor 20, 25. The instructions include instructions readable and executable by the server 25 to optimize a radiation therapy treatment for delivery by the LINAC 12 to a patient. The optimized radiation therapy treatment plan 30 can be saved to the one or more non-transitory storage media 26, transmitted (e.g., wirelessly) to the controller computer 18 of the LINAC 12 to control the LINAC 12 to deliver radiation therapy to the patient according to the optimized radiation therapy plan 30.

The non-transitory storage medium 26 stores instructions which are readable and executable by at least one electronic processor (e.g. the server 25) to perform disclosed operations including performing a radiation therapy plan optimization method or process 102 to generate the RT plan 30.

With continuing reference to FIG. 1, an illustrative embodiment of the radiation therapy plan optimization method 102 is diagrammatically shown as a flowchart. At an operation 104, a coarse resolution for the MLC is set. This may be a coarse resolution along the direction of the MLC leaf pair, and/or a coarse resolution in the "vertical" direction, that is, the direction transverse to the direction of the MLC leaf pair. By a "coarse" resolution, it is meant that the resolution is coarser than the physical resolution of the MLC 14. For the direction of the MLC leaf pair, the resolution is coarse in that the resolution for positioning of the leaf tips is not as fine as can actually be achieved by the mechanical actuators that move the leaves. For example, if the MLC 14 can actually position its leaf tips with a precision of 1.0 mm, then a coarse resolution might only allow for positioning the leaf tips with a precision (i.e. coarse resolution) of 5.0 mm. For the direction transverse to the MLC leaf pair (i.e. the "vertical" direction), the resolution is coarse in that the MLC 14 is modeled as having fewer leaf pairs than are actually present in the MLC 14. For example, if the MLC 14 has 40 leaf pairs then it might be represented with a coarse resolution of only 10 leaf pairs. This entails modeling groups of four-leaf pairs as a single leaf pair. In general, the operation 104 may set a coarse resolution only in the direction of the leaf pairs, or only in the direction transverse to the leaf pairs, or both. (If a coarse resolution is not used in one of those directions, then the full resolution achievable by the MLC 14 is employed in that direction).

In an operation 106, MLC optimization is performed using the coarse resolution defined at 104. The MLC optimization 106 may employ any known MLC optimization algorithm, and the MLC optimization 106 may be performed with respect to a fluence map generated by a prior FMO in which case the coarsened MLC settings are optimized with respect to an objective defined by the fluence map; or, the MLC optimization 106 may be performed with respect to a clinical objective, for example as is done in DMPO.

After the MLC optimization 106, in an operation 108 a finer MLC resolution is set compared with the initial coarsened resolution of operation 104. For example, if the MLC leaf tips have a physically realizable resolution of 1.0 mm and the coarse resolution at 104 is initially 5.0 mm then at operation 108 this may be reduced to 2.0 mm resolution (which is still coarsened compared with the physical resolution of 1.0 mm, but is finer than the initial 5.0 mm resolution). In addition to using a finer resolution, it is contemplated to reduce the optimization range: for example, if the initial optimization of the leaf tip positions was performed over the full dynamic range of the MLC 14, the operation 108 may now optionally set the range of one-half of the full range, centered (for each leaf tip) at the position of that leaf tip output by the MLC optimization 106. Likewise, if the MLC 14 has 40 leaf pairs and the initial coarsened resolution is 10 leaf pairs then at operation 108 this may be adjusted to 20 leaf pairs. As diagrammatically indicated by return arrow 110, flow then passes back to a next iteration of the MLC optimization 106 which is now performed at the finer resolution(s) set at operation 108. This loop 106, 108, 110 may optionally be repeated one or more times until at the last pass of operation 108 the resolution(s) are set equal to the physically achievable resolution of the MLC 14. In another contemplated variant not shown in FIG. 1, it is further contemplated to include successive reduction in angular resolution of the CPs along the arc, in addition to successive resolution of the MLC settings as per operations 104, 108.

At 102, MLC settings of the MLC 14 are optimized respective to an objective function, e.g. as described above. The MLC settings define tip positions of the MLC leaves 18 for a plurality of rows of MLC leaf pairs at a plurality of CPs along the arc. The optimizing 106 is performed in two or more iterations with a resolution of the MLC settings increasing per operation 108 in successive iterations. In one example, the objective function is defined by an optimized fluence map using FMO. The optimizing includes optimizing a fluence map by optimizing beamlets at the CPs along the arc respective to clinical objectives of the radiation therapy plan 30 (e.g., the clinical objectives including a minimum number of leaf 18 pairs in an opening, a minimum opening width, a smoothness of an opening, and a shape of an opening, among others). In another example, the objective function comprises clinical objectives of the radiation therapy plan 30 (e.g., a DPMO optimization loop).

In one embodiment, the optimizing operation 102 includes increasing a resolution of the positions of the tips of the leaves 18 of the MLC 14 in successive iterations. For example, in a first iteration, the positions of the tips of the leaves 18 are optimized over a coarse grid. In each succeeding iteration, the positions of the tips of the leaves 18 are optimized over a finer grid than the previous iteration until a mechanical resolution of the MLC leaf tips is reached. Optionally, the optimizing may further include reducing a range over which the leaf tip positions are optimized in successive iterations (e.g., the range may be the full mechanical range of the leaf tips in the first iteration, then in the second iteration may be +/−half that range respective to the position from the first iteration, etc.).

This embodiment of the optimizing operation 102 executes a pattern-matching process repeatedly at multiple iterations with a gradually-adjusted MLC grid spatial resolution. The first iteration described above is computationally efficient because the pattern-matching process is performed on a small set of hypothetical positions of the leaves 18 defined on the coarse MLC grid. In each succeeding iteration, a resulting opening between the leaves 18 is utilized to confine a search space for the pattern-matching process in the next iteration (i.e., the range over which the optimization is performed is reduced). Typically, such a restricted next-level search space is constructed as an interval of feasible openings that are "similar" to best matching opening in the current level. As used herein, "similarity" may refer to the spatial distance of corresponding leaf tip positions along a row dimension (e.g., a lateral length). The pattern matching in the next iteration searches over a new set of hypothetical openings that are defined on the fine MLC grid, but with imposing the additional search space restrictions that were derived from the outcome of the previous iteration. This optimizing operation 102 are executed over multiple iterations 106, 108, 110 until the sufficient final (physically realizable) resolution of the MLC grid has been reached. By such design, the number hypothetical openings between the leaves 18 to be evaluated in each iteration is kept under control, which limits the overall run-time.

The non-transitory storage media 26 store instructions to perform this embodiment of the optimizing operation 102. The instructions can include a set of levels of the leaves 18. The instructions also include instructions for generating a "best-fitting" multi-row pairings of openings between the leaves 18 by performing a match against, for example, a given target fluence. These instructions can impose local range constraints (or other segment opening requirements) to the individual leaf tips. A shortest path search algorithm can be implemented to determine the global optimal opening within the range constraints. The instructions can further include instructions for generating local position range constraints for leaf tip positions in each row of the MLC 14. The leaf tip positions of a given reference opening between the leaves 18 is used to construct range constraints in each row that define a (symmetric) spatial neighborhood around each given tip position. In general, the spatial width of each range might be selected by the user. However, a suitable choice is to set the left and right extent of the intervals equal to the MLC grid spacing of the currently considered iteration.

FIG. 2 shows an example of the first embodiment of the optimization operation 102. In this illustrative example, it is assumed that the hierarchical opening creation is executed e.g. in 3 different levels (i.e., three passes of the loop 106, 108, 110). The MLC 14 has a physically realizable resolution denoted by PRR (e.g., 1 mm as an example) in FIG. 2. The first level makes use of an MLC grid of a first resolution RES1 (e.g. 5 mm grid point spacing) and optimizes the leaf position only to the first resolution. The subsequent second and third levels shown in FIG. 2 make use of continuously increasing MLC grid resolutions, for example RES2 for the second level (e.g., a 2 mm grid spacing, and RES3 for the third level (e.g., a 1 mm grid spacing). More generally, the spatial resolution at the final level can be determined by considering both: (i) mechanical specifications of the MLC and (ii) parameters specified by the user or by the TPS.

A single leaf 18 of a leaf pair is shown in FIG. 2. (That is, the opposing leaf of the leaf pair is not shown in FIG. 2). Around the leaf tip positions in each row of the opening in each iteration, a travel range is defined over which the optimization is performed, (e.g., a travel range TR1 for the first iteration, which is equal to the full leaf travel range, a reduced travel range TR2 for the second iteration, and a further reduced travel range TR3 for the final iteration). Stated another way, the travel range TR1, TR2, and TR3 for each iteration is a constraint on the optimization. In each iteration after the first iteration, the travel range TR2, TR3 is centered at the last leaf tip position obtained by the previous iteration (for example, the travel range TR2 is centered at the leaf tip position obtained in the first iteration) and extends to both lateral sides (e.g., to the left and to the right) of the last tip position by a certain quantity. In illustrative FIG. 2, the travel range TR2 extends to the left by the previous coarse resolution RES1 and also to the right by RES1. Similarly, the travel range TR3 for the final iteration extends to the left by the previous coarse resolution RES2 and also to the right by RES2 until it reaches a resolution RES3 (which is equal to the physically realizable resolution PRR).

Referring back to FIG. 1, in another embodiment (optionally combinable with the first embodiment), the optimizing operation 102 includes increasing a number of rows of pairs of leaves 18 of the MLC 14 in successive iterations. That is, the resolution of the MLC settings in a "vertical" direction is increased. For example, in a first iteration, a number of rows of pairs of leaves 18 of the MLC 14 is reduced compared with a physical number of rows of MLC leaf pairs in the MLC by grouping adjacent leaf rows such that the MLC settings are optimized over a coarse grid in a direction transverse to the rows. In each succeeding iteration, the rows of leaves 18 are grouped using a finer grid until the physical number of rows of the MLC leaf pairs in the MLC is reached. This approach also helps to find an optimum (e.g., a local optimum) that adheres to the requirement, for instance to have segment openings with a minimum number of leaf pairs or segment opening. Smooth larger segment openings have a smaller difference between a computed dose and an actually delivered dose.

This embodiment of the optimizing operation 102 refers to the fast computation of a matching score of a single leaf pair against a row of the target fluence image. To obtain the optimal MLC opening that consists of multiple rows of leaf pair positions, such matching operation is carried out row-by-row, e.g. in a graph-search based optimization framework. This process can be further sped-up by executing the row matching operations in a hierarchical multi-resolution over the MLC rows in several levels: In other examples, a brute force evaluation of possible segment openings and approaches to cluster intensities (e.g., k-means) and convert those into segment openings.

FIG. 3 shows an example of the second embodiment of the optimizing operation 102. In a first level, the leaf pair matching operation is performed only for some pre-selected rows (e.g., rows 0 and 4 as shown in FIG. 3) depicted as black bars. For all the other rows (e.g., rows 1, 2, and 3, depicted as white bars), the leaf tip positions are set in an approximate, computationally cheaper (with respect to the leaf pair matching operation) manner. Such approximation of leaf positions might be e.g. based on interpolating from leaf tips in those pre-selected rows. Such interpolation also guides the opening generation towards smooth opening contour shapes that are favorable for accurate computation of patient radiation dose. The leaf pairs of all rows (matched or interpolated) resulting from this first level might be used in combination with the above mentioned hierarchical multi-level approach for leaf tip positioning, (e.g., shown in FIG. 2) with the resulting leaf tip positions are used to confine the search space for leaf positions for matching operations in the next level. Referring back to FIG. 3, in the second level, a different set of rows (e.g., rows 0, 2, and 4) is pre-selected which covers more rows then in the preceding level. Hence in the second level, more rows of leaf pairs are optimized accurately according to the matching operation, and fewer rows of leaf pairs (e.g., rows 1 and 3) are set by interpolation. This procedure is iterated over multiple levels until the leaf tip positions of all rows in the MLC are optimized by the matching operation (e.g., rows 0-4 as shown in the final level).

With continuing reference to FIG. 3, in another approach adjacent rows can be grouped together to form a single virtual row of greater width in the "vertical" direction transverse to the rows. This is shown diagrammatically by dashed boxes in the middle example of FIG. 3, where two virtual leaves 18v are indicated by dashed lines. This approach eliminates the computational cost of interpolation, but may be less effective at smoothing the opening contour.

In some examples, the optimizing operation 102 can include both increasing a resolution of the positions of the tips of the leaves 18 in successive iterations (e.g., as shown in FIG. 2) and increasing a number of rows of MLC leaf pairs in successive iterations (e.g., as shown in FIG. 3).

In a further aspect, the approach 102 of gradually increasing the resolution of the MLC settings can be combined with gradually increasing the resolution of (or otherwise controlling a number of) the angular positions of the CPs along the arc. This embodiment is particularly suitable for VMAT, which is based on arcs consisting of multiple sequential control points. Openings are generated for CPs positioned at different angular resolutions along the sequential (i.e. angular) dimension. In conventional (i.e. non-multi resolution) VMAT, the entire set of CPs along the arcs are simultaneously optimized, e.g. by application of the matching operation. Typically, such creation of all control points along the arcs is iterated multiple times in order to achieve a gradual refinement of the fitting fidelity to the target fluence.

In this embodiment, only few CPs (i.e. those defined at a coarse angular resolution) on the VMAT arcs are created by the matching operation. All other CPs are set by using a computationally cheap method. Such a computationally cheap method might be based on copying or interpolating from those openings created on the coarse angular resolution. Hence, the computationally expensive matching operations are initially only performed on the few CPs defined by the coarse angular resolution. In subsequent iterations, the resolution of the angular spacing is gradually increased such that a larger number of CPs becomes subject to the computationally expensive matching operation. Dose computations can be done during this process with a larger set of CPs (which may or may not be interpolated) to avoid inaccuracies.

The non-transitory storage media 26 stores instructions to perform this embodiment of the optimizing operation 102. These instructions can include angular resolutions of CPs along the VMAT arcs. The first iteration with a coarse angular spacing, which gets gradually finer up to the final angular CPs spacing. The instructions also include instructions for generate best fitting leaf pair openings at specific control points on the arc by performing a match against the given target fluence. For VMAT, these instructions are capable of imposing dynamic sequence constraints to the individual leaf tips. The instructions further include instructions to create synthetic leaf pair openings from other openings in the sequence. This is performed in a computationally efficient way. This might be realized, for example, by i) copying the closest (i.e., in an angular sense) existing opening from the sequence; ii) suitable interpolation from some existing openings in the sequence, etc.

FIG. 4 shows an example of iterative increase in angular resolution. In a typical VMAT optimization, the continuous arc is discretized to a resolution of control points along the arc with 4° angular spacing. For an illustrative multi-resolution approach, there are three levels of angular resolution: 16° for first level; 8° for second level; 4° for third level. FIG. 4 shows various angles of the leaves 18 along the CPs at angles at degrees of 0, 4, 8, 12, 16, 20, 24, and 32, labeled as A-H, respectively. Based on this example, in the first iteration step the openings (e.g., 0°, 16°, and 32°) are generated by application of the matching operation (as indicated by dark shading), while the openings at, for example, 4°, 8°, 12°, and 20° are synthesised cheaply from the other openings (as indicated by no shading). In a second iteration step, the openings at 0°, 8°, 16°, 24°, and 32° are generated by application of the matching operation, while the openings at 4°, 12°, 20°, and 24° are synthesised cheaply from the other openings. In a third iteration step, all openings are generated at the native angular spacing of 0°, 4°, 8°, 12°, 16° (and so forth) by application of the matching operation.

With reference back to FIG. 1, after the radiation treatment plan 30 is optimized, it is stored in the non-transitory storage 26. On the day of the radiation therapy session, the radiation treatment plan 30 is retrieved from the storage 26 to the workstation 18 and used to control the LINAC 12 to deliver radiation therapy according to the plan 30 including configuring the MLC 14 at each CP to deliver therapeutic radiation to the patient using the LINAC 12 traversing the arc while modulated by the MLC in accordance with the optimized radiation therapy plan 30.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

What is claimed is:

1. A device for optimizing a radiation therapy plan for delivering therapeutic radiation to a patient using a therapeutic radiation source while modulated by a multi-leaf collimator (MLC), the device comprising:
   at least one electronic processor connected to a radiation therapy device; and
   a non-transitory computer readable medium storing instructions readable and executable by the at least one electronic processor to perform a radiation therapy plan optimization method, the method comprising:
   optimizing MLC settings of the MLC respective to an objective function wherein the MLC settings define MLC leaf tip positions for a plurality of rows of MLC leaf pairs at a plurality of control points (CPs),
   wherein: the optimizing is performed in two or more iterations with a resolution of the MLC settings increasing in successive iterations; and the optimizing comprises reducing a travel range of the leaf tip positions and increasing a resolution of the leaf tip positions within the reduced travel range in the successive iterations.

2. The device of claim 1, wherein the optimizing comprises:
   in a first iteration, optimizing the MLC leaf tip positions over a coarse grid; and
   in succeeding iterations, optimizing the MLC leaf tip positions over a finer grid than the last iteration until a mechanical resolution of the MLC leaf tips is reached.

3. The device of claim 1, wherein the optimizing further comprises reducing a range constraint on the leaf tip positions in successive iterations.

4. The device of claim 1, wherein the optimizing comprises increasing a number of rows of MLC leaf pairs in successive iterations.

5. The device of claim 4, where the optimizing further comprises:
in a first iteration, reducing the number of rows of MLC leaf pairs compared with a physical number of rows of MLC leaf pairs in the MLC by grouping adjacent leaf rows such that the MLC settings are optimized over a coarse grid in a direction transverse to the rows; and
in succeeding iterations, grouping the leaf rows using a finer grid until the physical number of rows of the MLC leaf pairs in the MLC is reached.

6. The device of claim 4, where the optimizing further comprises:
in a first iteration, reducing the number of rows of MLC leaf pairs compared with a physical number of rows of MLC leaf pairs in the MLC by selecting a sub-set of the leaf rows and interpolating unselected rows between the selected rows of the sub-set such that the MLC settings are optimized over a coarse grid in a direction transverse to the rows; and
in succeeding iterations, increasing the number of rows in the selected sub-set until the physical number of rows of the MLC leaf pairs in the MLC is selected.

7. The device of claim 1, wherein the optimizing comprises controlling a number of angular positions of the CPs along a trajectory comprising an arc.

8. The device of claim 1, wherein the radiation therapy plan optimization method further comprises:
optimizing a fluence map by optimizing beamlets at the CPs along a trajectory comprising an arc respective to clinical objectives of the radiation therapy plan; and
wherein the objective function is defined by the optimized fluence map.

9. The device of claim 1, wherein the objective function comprises clinical objectives of the radiation therapy plan, the clinical objectives comprising a minimum number of leaf pairs in an opening, a minimum opening area, a smoothness of an opening, and or other characteristics of the shape of an opening.

10. The device of claim 1, further comprising a radiation therapy device configured to deliver therapeutic radiation to the patient using the therapeutic radiation source of the radiation therapy device traversing a trajectory comprising arc while modulated by the MLC in accordance with a radiation therapy plan optimized by the radiation therapy plan optimization method;
wherein the traversing of the trajectory comprises moving the therapeutic radiation source along the arc.

11. A non-transitory computer readable medium storing instructions executable by at least one electronic processor to perform a radiation therapy plan optimization method, the method comprising:
optimizing multi-leaf collimator (MLC) settings of an MLC of a radiation therapy device respective to an objective function wherein the MLC settings define MLC leaf tip positions for a plurality of rows of MLC leaf pairs at a plurality of control points (CPs) along an arc,
wherein the optimizing is performed in two or more iterations with a resolution of the MLC settings increasing in successive iterations; and the optimizing comprises reducing a travel range of the leaf tip positions and increasing a resolution of the leaf tip positions within the reduced travel range in the successive iterations.

12. The non-transitory computer readable medium of claim 11, wherein the optimizing comprises:
in a first iteration, optimizing the MLC leaf tip positions over a coarse grid; and
in succeeding iterations, optimizing the MLC leaf tip positions over a finer grid than the last iteration until a mechanical resolution of the MLC leaf tips is reached.

13. The non-transitory computer readable medium of claim 11, wherein the optimizing further comprises reducing a range constraint on the leaf tip positions in successive iterations.

14. The non-transitory computer readable medium of claim 11, wherein the optimizing further comprises increasing a number of rows of MLC leaf pairs in successive iterations.

15. The non-transitory computer readable medium of claim 14, where the optimizing further comprises:
in a first iteration, reducing the number of rows of MLC leaf pairs compared with a physical number of rows of MLC leaf pairs in the MLC by grouping adjacent leaf rows such that the MLC settings are optimized over a coarse grid in a direction transverse to the rows; and
in succeeding iterations, grouping the leaf rows using a finer grid until the physical number of rows of the MLC leaf pairs in the MLC is reached.

16. The non-transitory computer readable medium of claim 11, wherein the optimizing comprises optimizing angular positions of the CPs along the arc.

17. The non-transitory computer readable medium of claim 11, wherein the radiation therapy plan optimization method further comprises:
optimizing a fluence map by optimizing beamlets at the CPs along the arc respective to clinical objectives of the radiation therapy plan;
wherein the objective function is defined by the optimized fluence map.

18. The non-transitory computer readable medium of claim 11, wherein the objective function comprises clinical objectives of the radiation therapy plan.

19. A radiation therapy plan optimization method, comprising:
optimizing multi-leaf collimator (MLC) settings of an MLC of a radiation therapy device respective to an objective function wherein the MLC settings define MLC leaf tip positions for a plurality of rows of MLC leaf pairs at a plurality of control points (CPs) along the arc; and
delivering therapeutic radiation to the patient using a therapeutic radiation source of the radiation therapy device traversing the arc while modulated by the MLC in accordance with a radiation therapy plan;
wherein: the optimizing is performed in two or more iterations with a resolution of the MLC settings increasing in successive iterations; and the optimizing comprises reducing a travel range of the leaf tip positions and increasing a resolution of the leaf tip positions within the reduced travel range in the successive iterations.

* * * * *